US009513193B2

(12) United States Patent
Olmedo et al.

(10) Patent No.: US 9,513,193 B2
(45) Date of Patent: Dec. 6, 2016

(54) SOFT SOIL SAMPLING DEVICE AND SYSTEM

(71) Applicants: Nicolas Olmedo, Edmonton (CA); Stephen Dwyer, Edmonton (CA); Michael Lipsett, Edmonton (CA); James Yuen, Calgary (CA)

(72) Inventors: Nicolas Olmedo, Edmonton (CA); Stephen Dwyer, Edmonton (CA); Michael Lipsett, Edmonton (CA); James Yuen, Calgary (CA)

( * ) Notice: Subject to any disclaimer, the term of this patent is extended or adjusted under 35 U.S.C. 154(b) by 188 days.

(21) Appl. No.: 14/569,556

(22) Filed: Dec. 12, 2014

(65) Prior Publication Data

US 2016/0169772 A1 Jun. 16, 2016

(51) Int. Cl.
| | |
|---|---|
| *G01N 1/08* | (2006.01) |
| *D21G 9/00* | (2006.01) |
| *G01N 1/20* | (2006.01) |
| *G01N 1/12* | (2006.01) |
| *E21B 49/02* | (2006.01) |

(52) U.S. Cl.
CPC ........ *G01N 1/08* (2013.01); *D21G 9/00* (2013.01); *E21B 49/02* (2013.01); *G01N 1/12* (2013.01); *G01N 1/20* (2013.01)

(58) Field of Classification Search
CPC ....................................................... G01N 1/08
USPC ....................................................... 73/864.32
See application file for complete search history.

(56) References Cited

U.S. PATENT DOCUMENTS

| | | | | |
|---|---|---|---|---|
| 3,805,900 A | * | 4/1974 | Sainsbury | E21B 25/04 175/20 |
| 3,962,922 A | * | 6/1976 | Takeuchi | G01N 1/20 73/215 |
| 3,977,479 A | * | 8/1976 | Sainsbury | E21B 1/02 173/185 |

(Continued)

FOREIGN PATENT DOCUMENTS

CN 86205547 * 5/1987 ............. E21B 49/02

OTHER PUBLICATIONS

C.R.I. Clayton, M.C. Matthews & N.E. Simons, 'Site Investigation', Department of Civil Enginneering, University of Survey, http://www.geotechnique.info/, 2nd Edition, 1995, Chapter 7, 32 pages.*

(Continued)

*Primary Examiner* — David Gray
*Assistant Examiner* — Kevin Butler
(74) *Attorney, Agent, or Firm* — Timothy Marc Shropshire; Garrett James O'Sullivan; MU Patents

(57) ABSTRACT

A sampling device for retrieving a sample having a frame, a scoop with an open end configured to retrieve a sample, an actuator in communication with the scoop, a base plate mounted below the frame, configured to support the sampling device on the material, and a spade at least as large as the opening, extending below the base plate, configured to extend into the material and configured to engage with the open end of the scoop once a sample has been retrieved, wherein the actuator is configured to move the scoop between an open and a closed position, and in the open position, there is a gap between the open end of the scoop and the spade for the entry of a sample, and in the closed position, the open end of the scoop sealingly engages with the spade to close the scoop and retain the retrieved sample.

20 Claims, 15 Drawing Sheets

(56) References Cited

U.S. PATENT DOCUMENTS

| | | | | |
|---|---|---|---|---|
| 3,978,932 A * | 9/1976 | Mielke | | E21B 7/26 175/243 |
| 4,304,139 A * | 12/1981 | Johnson | | G01N 1/04 73/864.32 |
| 4,456,079 A * | 6/1984 | Rassieur | | E21B 7/002 175/171 |
| 5,322,133 A * | 6/1994 | Hart | | B25D 1/16 175/20 |
| 5,385,059 A * | 1/1995 | Varouxis | | G01N 1/12 175/20 |
| 5,474,141 A * | 12/1995 | Hart | | B25D 1/16 175/20 |
| 5,488,876 A * | 2/1996 | Casey | | E21B 33/127 73/864.44 |
| 6,016,713 A * | 1/2000 | Hale | | A01B 79/005 73/864.45 |
| 2004/0042884 A1* | 3/2004 | Jester | | A63B 47/021 414/501 |
| 2009/0205446 A1* | 8/2009 | Lyman | | G01N 1/08 73/863.91 |
| 2014/0095074 A1* | 4/2014 | Covely | | G01N 1/08 702/2 |
| 2015/0344136 A1* | 12/2015 | Dahlstrom | | B64C 39/024 701/3 |
| 2015/0377405 A1* | 12/2015 | Down | | G05D 1/102 73/865.8 |
| 2016/0018224 A1* | 1/2016 | Isler | | G01C 21/005 701/25 |
| 2016/0157414 A1* | 6/2016 | Ackerman | | A01B 69/008 701/25 |
| 2016/0169772 A1* | 6/2016 | Olmedo | | G01N 1/08 73/864.32 |

OTHER PUBLICATIONS

New York State Department Enviromental Conservation, '3.0 Sampling Equipment', http://www.dec.ny.gov/docs/remediation_hudson_pdf/sgpsect3.pdf, Jun. 1, 2010, 35 Pages.*

* cited by examiner

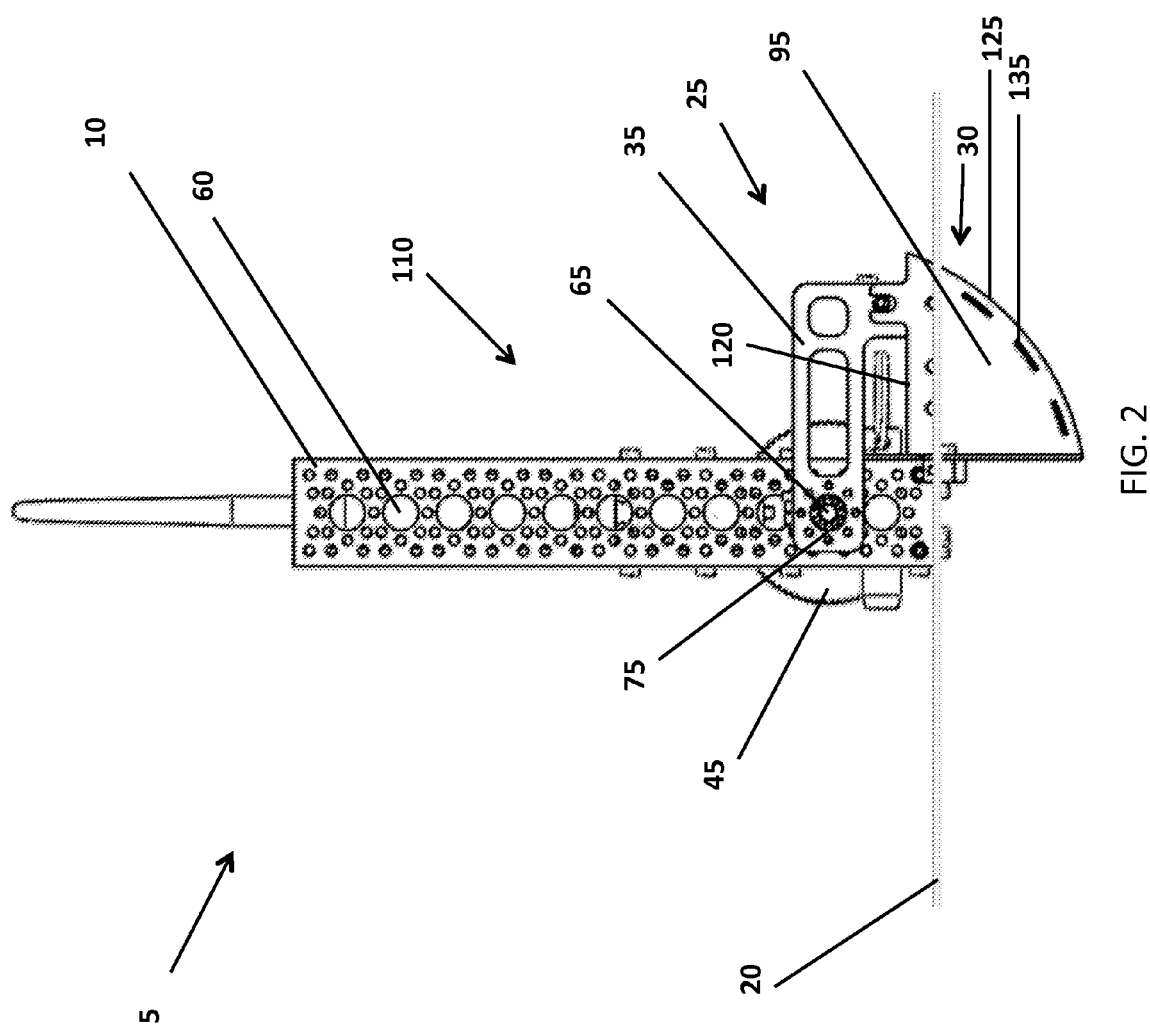

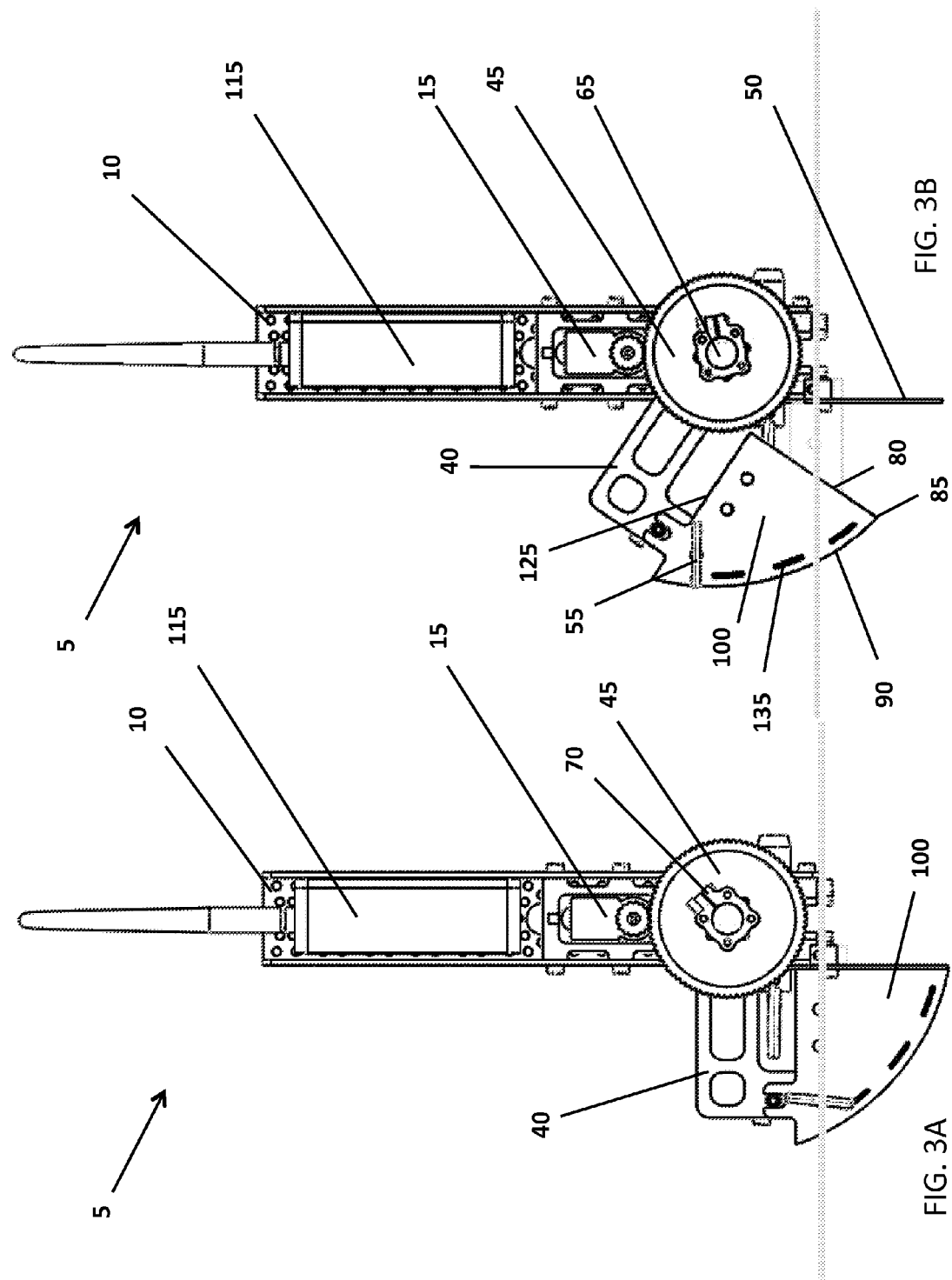

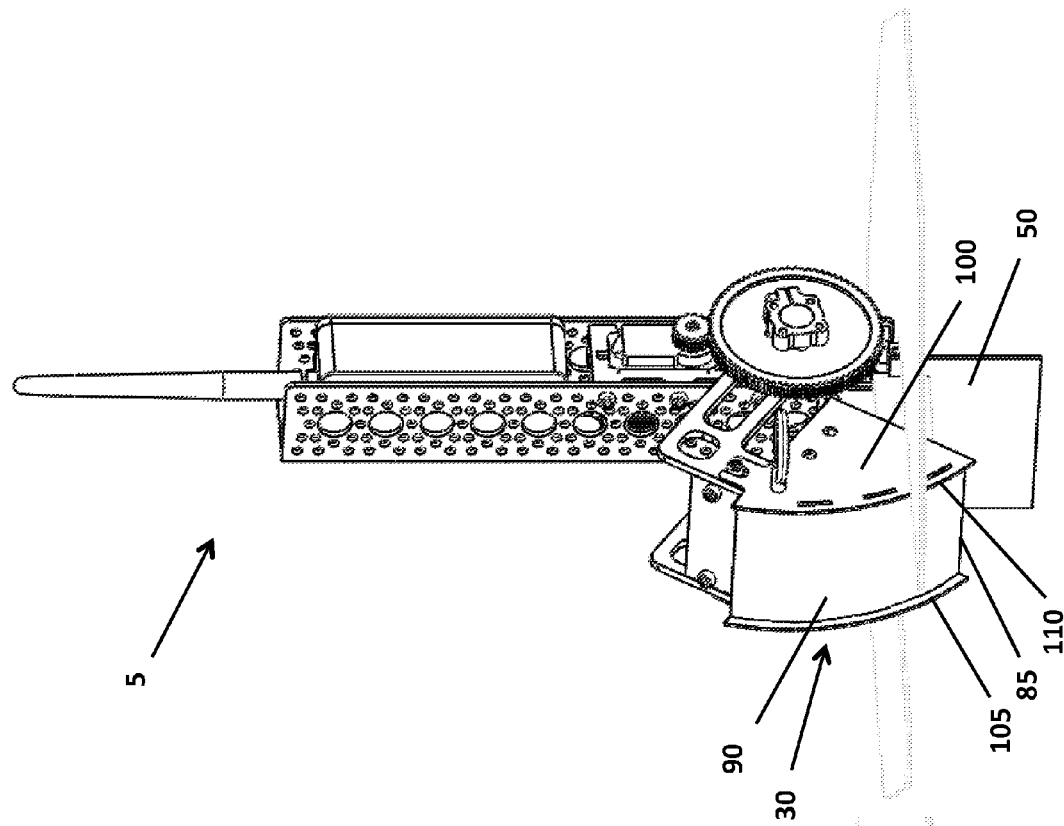
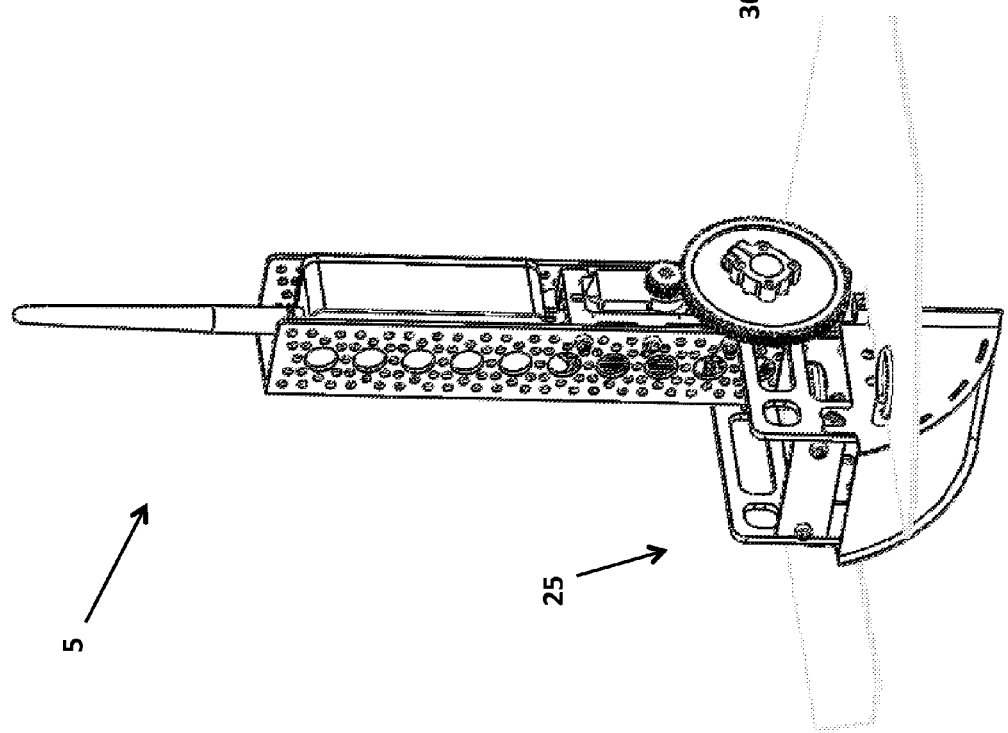

SOFT SOIL SAMPLING DEVICE AND SYSTEM

FIELD OF THE INVENTION

The present invention relates to a deployable sampling device for collecting soil, earth, and other samples in various regions, more particularly in regions where the soil has low bearing strength.

BACKGROUND OF THE INVENTION

Starting in the 20th Century, Alberta, Canada and its mining companies have strived towards the development of cleaner energy and the reclamation of regions affected by resource extraction. The most important areas that are affected by the mining industry are tailings ponds created by the storage of waste materials after mineral extraction. Obtaining useful data regarding how these materials respond to reclamation efforts is the key towards developing faster and more reliable methods of reclamation.

To date, sampling has been performed using specialized hand tools and rovers. Using hand tools for collection is often difficult and expensive because the majority of tailings do not yield enough bearing strength to support a human's weight. In an attempt to further sampling efforts in regions of tailings with lower bearing strengths, autonomous terrestrial samplers have been developed. Unfortunately, the rover, being the primary vehicle for autonomous terrestrial sampling, is still too heavy for many regions requiring sampling. As a result, large portions of tailings ponds cannot be effectively examined.

Oftentimes, regions of settled tailings are inaccessible by land due to the low bearing strength of the tailings. In the regions of 0 to 30 kPa, the tailings pond surface becomes very soft and sludgy. As a result, it is very difficult for surveyors and their equipment to avoid becoming stuck while operating. With the recent developments in embedded systems and wireless communications, robotics have become an opportune means for monitoring in these regions.

Unmanned aircraft systems (UAS) are becoming increasingly popular in a variety of industrial applications. In the past, UAS have been deployed to monitor industrial sites in a variety of capacities. UAS provide a significant benefit of being able to hover above the ground in a single location, preventing any disturbance of the ground below. Additionally, a multi-rotor or helicopter UAS possesses superior stability, maneuverability, and the capacity to carry a significant payload. To date, UAS have not been utilized for soil sample collection for monitoring reclamation activities.

Based on the foregoing, there is a need in the art for a sampling device that works in combination with UAS technology to deploy the sampling device, allowing efficient and reliable collection of samplings. In addition, there is a need for a sampling device to be deployed from an existing multicopter platform, with an easily replaceable sampler holder, that can access regions of settled tailings that are not approachable on ground due to low bearing strength of the soft tailings.

SUMMARY OF THE INVENTION

In the present invention, a sampling device for retrieving a sample is presented having a frame, a scoop with an opening configured to retrieve a sample, an actuator in communication with the scoop, a base plate mounted below the frame, configured to support the sampling device on the material, and a spade at least as large as the opening, extending below the base plate, configured to extend into the material and configured to engage with the opening of the scoop once a sample have been retrieved, wherein the actuator is configured to move the scoop between an open and a closed position, and in the open position, there is a gap between the open end of the scoop and the spade for the entry of a sample, and in the closed position, the open end of the scoop sealingly engages with the spade to close the scoop and retain the retrieved sample.

In an embodiment, the sampling device may have a shaft, and at least one moment arm, each moment arm having a first end and a second end, wherein the first end is attached to the scoop and the second end is attached to the shaft, wherein the actuator rotates the shaft, causing the moment arm(s) to move the scoop between the open and closed positions.

In an embodiment, the sampling device may have an unmanned aerial vehicle; and a tether connecting the aerial vehicle and the sampling device, wherein the unmanned aerial vehicle is configured to transport the sampling device to areas of low soil bearing strength, where it deploys and retrieves the sampling device using the tether.

In an embodiment, the sampling device may have an unmanned aerial vehicle; and a winch, attached to the unmanned aerial vehicle, wherein the unmanned aerial vehicle is configured to transport the sampling device to areas of low soil bearing strength, where it deploys and retrieves the sampling device using the winch.

In an embodiment, the sampling device may have an antenna attached to the sampling device, an antenna attached to the unmanned aerial vehicle; and a radio-frequency-enabled remote ground station, wherein the sampling device, the unmanned aerial vehicle, and the ground station communicate with one another through radio frequency.

In an embodiment, the sampling device may have rubber protrusions affixed to the spade that correspond with the open end of the scoop.

In an embodiment, the base plate of the sampling device may have cut-outs configured for reducing wind resistance.

In an embodiment, the sampling device may have a suction-eliminating layer on the underside of the base plate, the layer selected from the group consisting of a rubber membrane, a hydrophobic coating and a disposable paper liner. In an embodiment, at least a portion of the base plate is constructed of a lightweight and buoyant material.

In an embodiment, the sampling device may have one or more moment arms connected between the scoop and the actuator for rotating the scoop from an open to a closed position. In a preferred embodiment, the sampling device would have two moment arms.

In an embodiment, the scoop of the sampling device closes against the spade, forming a container. In a further embodiment, the container is removable from the sampling device. In a further embodiment, the container is self-enclosing.

In an embodiment, the sampling device may have a detachable cover on the bottom of baseplate, configured to reduce suction between the baseplate and the material. The detachable cover can be biodegradable.

In an embodiment, the sampling device may have an antenna that communicates with a ground station to signal the actuator to move the scoop.

In an embodiment, the sampling device can be aerially deployable and retrievable by an aircraft capable of hovering. In an embodiment, the sampling device is remotely deployable and retrievable from impassable locations, for example, due to low bearing strength soils.

The foregoing, and other features and advantages of the invention, will be apparent from the following, more particular description of the preferred embodiments of the invention, the accompanying drawings, and the claims.

BRIEF DESCRIPTION OF THE FIGURES

For a more complete understanding of the present invention, the objects and advantages thereof, reference is now made to the ensuing descriptions taken in connection with the accompanying drawings briefly described as follows.

FIG. 2 is a side elevation view of the sampling device, according to an embodiment of the present invention;

FIG. 3A is a side elevation view of the sampling device in the sample containment position, according to an embodiment of the present invention;

FIG. 3B is a side elevation view of the sampling device in the sample retrieval position, according to an embodiment of the present invention;

FIG. 4A is a perspective view of the sampling device in the sample containment position, according to an embodiment of the present invention;

FIG. 4B is a perspective view of the sampling device in the sample retrieval position, according to an embodiment of the present invention;

DETAILED DESCRIPTION

The present invention is a sampling device for soil, particularly soft soil and tailings ponds that takes a sample using a scoop, while hovering above the soft soil by a take-off/landing flying device. Samples, ranging from soil to tailings to liquid samples, are referred to throughout as soil samples.

Figure 1:
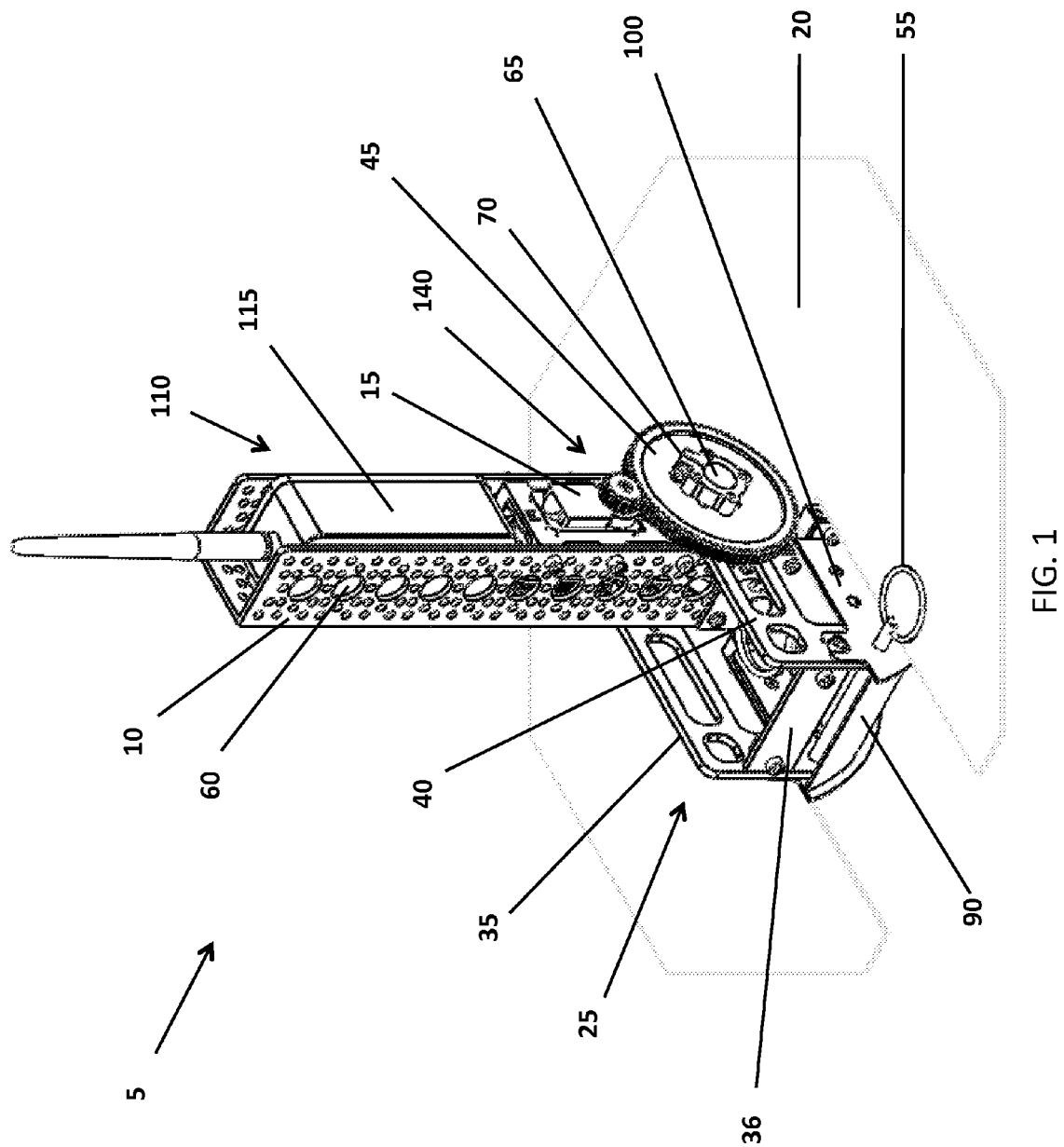
FIG. 1 is a perspective view of the sampling device, according to an embodiment of the present invention.
Figure 8:
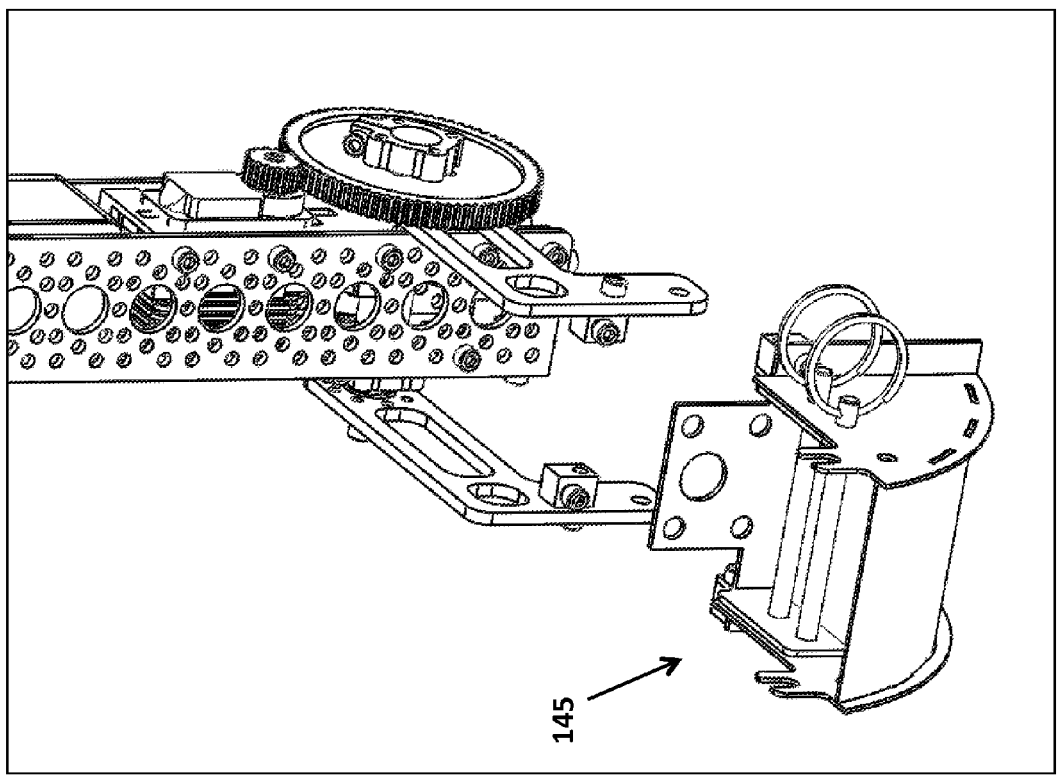
FIG. 8 is a perspective view of the lower portion of the sampling device, showing removal of the scoop and spade, according to an embodiment of the present invention.

With reference to FIGS. 1-2, the sampling device 5 comprises of a tower assembly 110 populated with a control system 115, a servo gearbox 15, a baseplate 20, a spade 50, and a scoop assembly 25. The control system 115 and servo gearbox 15 are generally located within tower 10. The scoop 30 is removably attached to two moment arms 35 and 40, which are connected to, and pivot with, a shaft 65. In a preferred embodiment, shaft 65 is one of a D-shaft a Double-D shaft, a splined shaft. The shaft 65 has a gear 45 mounted thereon, which is in communication with and rotated by servo gearbox 15. Acting as a penetrating point and balancing pillar, the spade 50 is attached to the bottom of tower 10, and extends generally downwards. Baseplate 20 is situated around tower 10 and above spade 50 to act as a landing plate or float to prevent sinking or tipping in wet samples, and especially during sample collection. The moment arms 35, 40 are connected near the ends of shaft 65 and pivot around the shaft axis as shaft 65 rotates. Moment arms 35, 40 rotate about the shaft axis to lift scoop 30 away from spade 50 when shaft 65 moves in an opening direction, and move the scoop 30 towards the spade 50, so that it closes flush against spade 50 in a closing direction. When servo 15 is commanded to actuate by the control system 115, it rotates the scoop 30 beneath the system to clamp flush against spade 50. In an embodiment, the servo 15 moves within a limited range. The spade 50 and scoop 30 act as a container 145 (see FIG. 8) in which the collected samples are contained, and in an embodiment the container is watertight to contain the sample when closed. The container 145 can then be separated from the sampling device using a quick release pin 55 located between the scoop 30 and the scoop arms 35, 40, once sampling device 5 is in the hands of the scientist or user.

With reference to FIGS. 3A, 3B, 4A and 4B, the sampler is movable between closed (shown in FIGS. 3A and 4A) and open (shown in FIGS. 3B and 4B) positions. Moment arms 35, 40 lift scoop 30 away from spade 50 when the shaft 65 moves in an opening direction, and moves scoop 30 towards the spade 50, so that it closes flush against spade 50 in a closing direction. When servo 15 is commanded to actuate by the control system 115, it rotates the scoop 30 beneath the system to clamp flush against the spade 50. In an embodiment the servo 15 moves within a limited range.

The closed position holds a sample within the container formed by scoop 30 and spade 50. To move to a closed position from an open position, servo 15 urges gear 45 to rotate shaft 65 in a closing direction. The shaft rotation moves moment arms 35, 40 to which it is attached in a downward direction. As scoop 30 is attached to the ends of moment arms 35, 40, scoop 30 moves downward, cutting through the soil sample as it moves to meet spade 50 in a flush, sealing arrangement, wherein scoop 30 and moment arms 35, 40 are generally horizontally oriented. When moving to an open position from a closed position, the rotation of shaft 25 is urged by servo 15 in the opposite direction. The moment arms 35, 40 move generally upward and scoop 30 rotates away from the spade 50, releasing contents contained within the scoop 30 if applicable.

Tower Assembly

With reference to FIGS. 1-2, tower assembly 110 comprises tower 10, a gear reduction system 140 which includes servo 15, control system 115, collar 75, ball bearing mounts 70, gear 45, and shaft 65. Tower 10 is a generally vertical channel or enclosure, with a hollow C-shaped body. In a preferred embodiment, tower 10 includes a plurality of mounting holes 60, of varying diameters, which allow for rigid mounting of all the components of the sampling device 5. In a preferred embodiment, tower 10 is made of aluminum, but it can be made of other materials as well such as plastic or carbon fiber, preferably perforated to reduce mass.

Servo 15 has a gearbox and a motor, wherein the motor rotates the gears. Servo 15 is in communication with shaft 65 through gear reduction system 140 and provides rotational force to rotate scoop 30. Servo 15 is generally mounted within tower 10, with gear 45 external to tower 10 in an embodiment. Servo 15 can be mounted by inserting bolt or screws through mounting holes 60 in tower 10. When servo 15 is commanded to actuate by control system 115, it rotates scoop 30 beneath the system to clamp flush against spade 50. In an embodiment servo 15 moves within a limited range. One example of a servo that may be used is the SPG5485A-CM-360 channel mount Servo Power Gearbox.

Figures 5A, 5B:
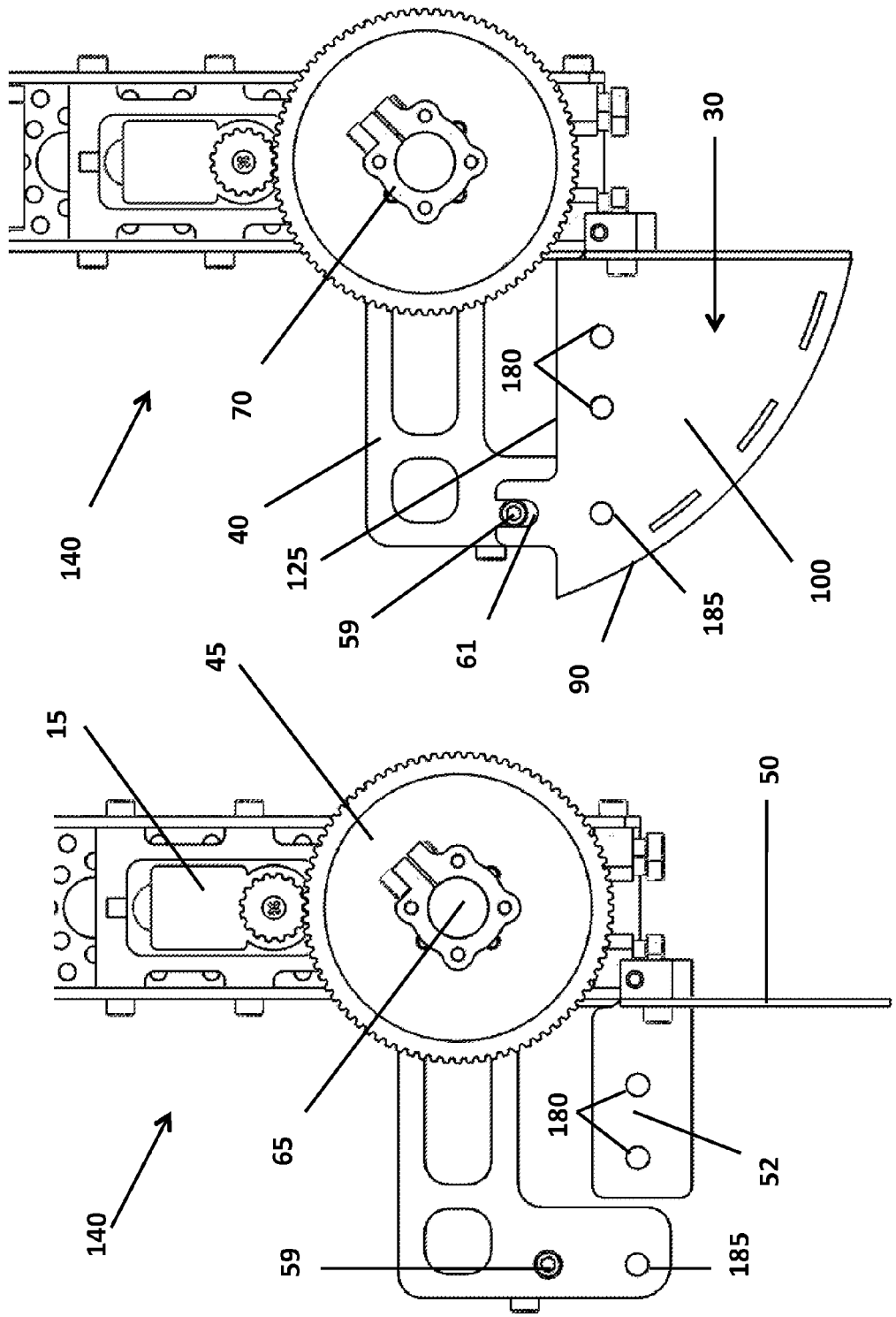
FIG. 5A is a side elevation view of the gear reduction assembly and scoop assembly without the scoop showing pinholes, according to an embodiment of the present invention.
FIG. 5B is a side elevation view of the gear reduction assembly and scoop assembly showing alignment of pinholes, according to an embodiment of the present invention.

With reference to FIGS. 5A and 5B, gear reduction system 140 is mounted mostly within tower 10 with gear 45 external to tower 10 in an embodiment. Gear reduction system 140 comprises gear 45, shaft 65, collar 75, and ball bearing mounts 70, as well as the servo 15. As servo 15 actuates gear reduction system 140 and it rotates gear 45 back and forth. Scoop shaft 65 can be inserted through a mounting hole 60 of the tower 10 and secured by placing collar 75 (see FIG. 2) on the end of shaft 65 so that collar 75 is positioned on the outside of the tower 10 and prevents gear 45 from slipping out of shaft 65. Ball bearing mounts 70 can be placed around shaft 65 and/or mounted internally within tower 10 to secure the position of shaft 65 and gear 45, as well as reduce the rotating friction of shaft 65. Gear 45 is placed on the opposing end of the shaft 65, which is in communication with the gear of servo 15. In an embodiment, ball bearings may be replaced by bushings for cost savings in materials.

Scoop Assembly

With reference to FIGS. 2, 3A, 3B, 4A, and 4B, the scoop assembly 25 has scoop 30, two scoop moment arms 35, 40 and shaft 65. Scoop 30 has an open end 80 with a cutting edge 85 for retrieving samples, a bottom 90 that curves upward and two vertical side plates 95 and 100, the side plates 95 and 100 each having an upper and lower edge 120 and 125, respectively. The side plates 95 and 100 extend upward from the bottom's curved edges 105 and 110, respectively, wherein the side plates' lower edges are fixedly attached near the scoop's bottom 90 along the entire length of its curve.

In one embodiment, the scoops bottom's 90 curved edges have teeth (not shown) extending outwardly from the sides for interlocking with side plates 95, 100. The side plates 95, 100 are joined to the bottom 90 using holes 135 in the side plates 95, 100 that correspond, and align, with the teeth (not shown), allowing scoop bottom 90 and side plates 95, 100 to interlock. In one embodiment, the scoop 30 is fortified and sealed along the interlocking teeth (not shown) and holes 135 using an industrial grade adhesive or rivets. In an embodiment, the bottom 90 and sides 95, 100 are formed as a single piece, by casting, molding or forming, for example. In an embodiment, welding and brazing are used to join the bottom 90 to the side plates 95, 100, forming the scoop 30.

In a preferred embodiment, moment arms 35, 40 are generally L-shaped and are fixedly attached to the side plates 95, 100 near the end of the scoop opposite the open end 80, wherein the moment arms 35, 40 extend above the scoop 30 and curve back toward the scoop's open end 80 to engage with the shaft 65. In a preferred embodiment, moment arms 35, 40 are constructed of aluminum plate, providing structural integrity while reducing payload weight. In an embodiment, moment arms 35, 40 are constructed of steel for enhanced strength or composite materials, such as carbon fiber sheets, to lower weight while keeping the same strength. In one embodiment, moment arms 35, 40 and other components are perforated to save weight.

In an embodiment, moment arms 35, 40 are generally C-shaped and are fixedly attached along the upper edge of the side plates, wherein the arms 35, 40 extend above the scoop 30 and curve back toward the scoop's open end 80 where they engage with the scoop shaft 65. The arms 35, 40 are removable and replaceable in case of becoming bent or worn. In an embodiment, a lateral support member 36 (see FIG. 1) can be included in scoop assembly 25 provide more support between arms 35, 40.

Shaft 65 is a generally cylindrical bar or pipe, having an engagement edge (not shown) that extends the entire length of the shaft 65. The engagement edge (not shown) of shaft 65 allows it to engage with the gear system 140 and moment arms 35, 40 without slippage, transmitting torque from gear reduction system 140 to moment arms 35, 40, which then transfers the torque to a force acting on scoop 65, allowing scoop 65 to close and retain a sample. In an embodiment, the engagement edge (not shown) is a flat portion running the length of the shaft 65, to prevent the gear 45 and moment arms 35, 40 from slipping around shaft 65.

In a preferred embodiment, scoop 30 is constructed of aluminum sheet metal. The malleability of this material allows the ideal radial curvature to be easily constructed. Additionally, payload weight is reduced compared using a material such as steel. In an embodiment, scoop 30 is constructed of stainless steel for ease of cleaning, while other materials may also be used such as plastic or composite materials in order to reduce weight while maintaining the same strength.

The motion of scoop 30 is radial around the axis of shaft 65. By having this curvature on scoop's bottom 90, the cutting edge 85 remains at a 90-degree angle to the soil surface, decreasing the degree of soil compaction and energy spent by servo 15. The scoop geometry acts as a storage receptacle for the sample with the scoop radius of curvature centered at the axis of rotation to minimize compaction during sampling.

Baseplate Assembly

With reference to FIG. 1, in a preferred embodiment, base plate 20 is a planar, octagonally- or circularly-shaped sheet of material, having a gap on one edge for receiving sampling device 5. In an embodiment, there is at least one hole (not shown) at a point at or near the center of base plate 20, to connect angle bracket(s) (not shown) that are attached to the base of the tower 10. In a preferred embodiment, 90 degree attachment blocks are used to connect baseplate 20 using that hole or holes. When sampling device 5 and base plate 20 are fully engaged, base plate 20 is fixedly attached to sampling device 5 using bolts, screws or some other fastening means inserted through the aligned holes (not shown).

In a preferred embodiment, a polycarbonate baseplate 20 is used for its properties that balance rigidity with flexibility. The flexibility serves as a cushion allowing forces to be dissipated throughout the plate, preventing shock to the sampling assembly and UAV, and adapting to soil surface contour. In an embodiment, base plate 20 is made of carbon fiber or plastic. In an embodiment, all or portions of the baseplate 20 can be made of extruded polystyrene foam to provide extra buoyancy.

Base plate 20 provides stability during sampling and limits sample plate penetration to correct depth. Additionally, base plate 20 protects sampling device 5 from tailings which it is sampling. Without base plate 20, the first and only point of contact is spade 50, concentrating the weight of sampling device 5 directly into a smaller area. As result, less soil bearing strength is available to prevent submersion. Furthermore, the tipping force is essentially zero. Base plate 20 prevents this occurrence by providing a larger surface area to distribute weight evenly.

Since the regions of interest within the tailing ponds vary between 0-30 kPa in bearing strength, safety measures must be taken to ensure that the sampler lands flat above the surface to prevent being submerged. To decrease the concentration of weight, base plate 20 is used to increase surface area. By having the sampler's weight spread across a larger region, the likelihood of sampling device 5 submerging is decreased.

In an embodiment, a rubber membrane (not shown) or a hydrophobic coating can be added to base plate 20 to decrease or eliminate suction created between base plate 20 and the soil or tailing pond surface, as the deploying device lifts off. In an embodiment, a detachable paper cover (not shown) can be added to the bottom of the base plate 20 to decrease or eliminate suction created between the base plate 20 and the soil or tailing pond surface, particularly when the surface is wet. In addition, the detachable paper cover can be biodegradable as to not leave materials behind.

In an embodiment, the base plate 20 has cut-outs (not shown) to reduce mass, and air and wind resistance, in effect, lessening power consumption by the sampling device 5 and allowing longer sampling missions.

Spade

Spade 50 serves as the initial point of contact with the sampling surface and provides stability during sampling. Further, it acts as a stopping surface, holding the sampler in a particular spot, onto which the scoop 30 closes to retain samples. The shape of the spade 50 corresponds generally to scoop 30's opening 80. In a preferred embodiment, spade 50 is generally flat and is connected to tower 10 by a pin and located by at least one bolt. Holes in the spade 50 align with bolts attached to tower 10 to prevent unwanted twisting. The pin keeps spade 50 generally flat against tower 10. In a preferred embodiment, spade 50 has two arms 51, 52 (see FIG. 5A, where spade arm 51 is located directly behind spade arm 52) that extend perpendicularly from the upper portion of the spade 50 parallel to the moment arms 35, 40. The spade's arms 51, 52 each have at least one hole that corresponds, and axially aligns, with a hole, or holes, in the side plates 95, 100, to secure scoop against the spade and retain the sample. In a preferred embodiment, spade 50 is constructed of a rigid, lightweight material, for example aluminum, capable of withstanding the sampler impact with a sampling surface. In an embodiment, rubber extrusions that correspond with the edges of the scoop's open end 80 are affixed to spade 50, allowing scoop 30 to engage with spade 50 upon closure, effectively increasing liquid sample retention. In an embodiment, spade 50 is L-shaped and connected to base plate 20.

Pins

With reference to FIGS. 5A through 8, removable pins 56, 57 can engage with corresponding, and axially aligned, holes 180 near the side plates' upper edges 120, 125 and the spade arms 51, 52 (see FIGS. 5A-6B). When the pins 56, 57 are inserted, scoop 30 becomes locked in a sample containment position 145, wherein the scoop 30 is retained against the spade 50 to contain the sample. To unlock scoop 30 and allow it to transition to the sample retrieval position, pins 56, 57 can be removed.

With reference to FIGS. 5A to 8, in a preferred embodiment, there is an additional pinhole and a U-shaped tab 61 for accommodating a screw, along the side plates' upper edges 120, 125 wherein another pin 55 passes through holes 185, used to attach scoop 30 to moment arms 35, 40 prior to sampling. The tab 61 above the hole 185 engages a screw 59 on the moment arms 35, 40 to maintain alignment. Scoop 30 moves with pivot of moment arms 35, 40 while remaining in fixed relationship with the moment arms 35, 40 due to the tab 61. After scoop 30 has rotated and enclosed a sample, pin 55 can be removed, and pins 56, 57 can be inserted into their respective holes 180, releasably locking scoop 30 and spade 50 together, permitting the container 145 to be detached.

Figure 6B:
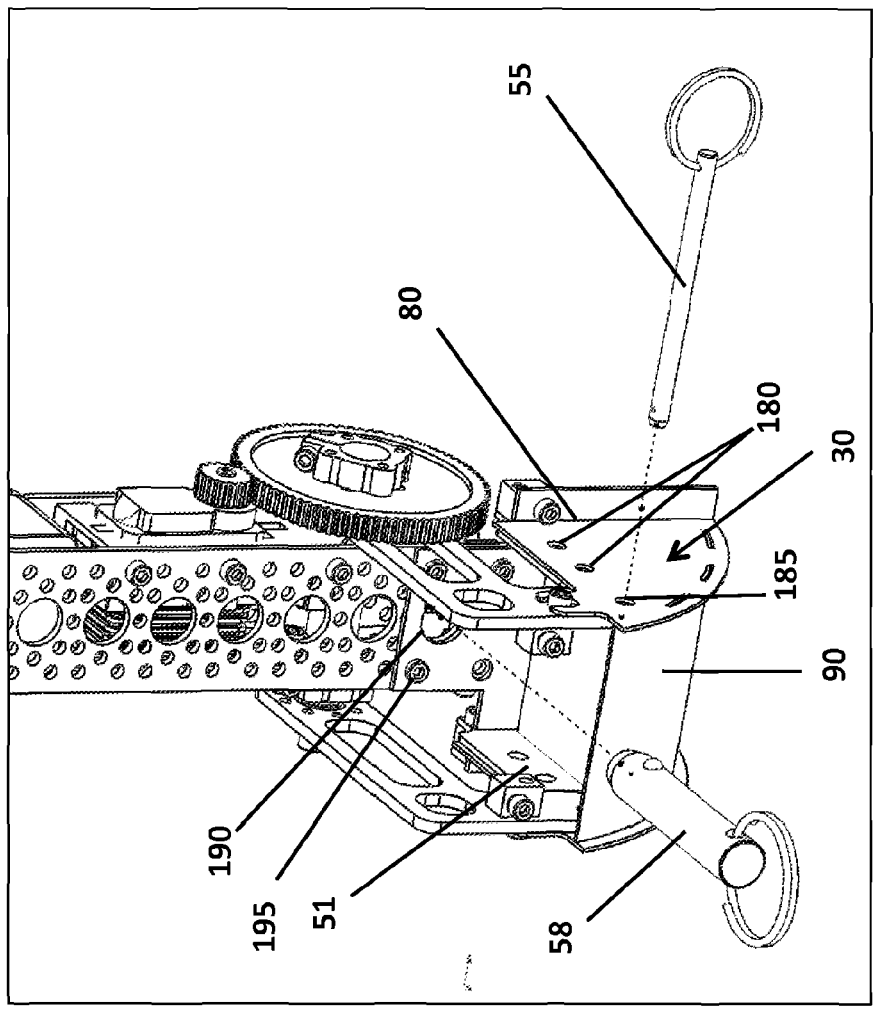
FIG. 6B is a perspective view of the lower portion of the sampling device, detailing pin placement for scoop activation, according to an embodiment of the present invention.
Figure 6A:
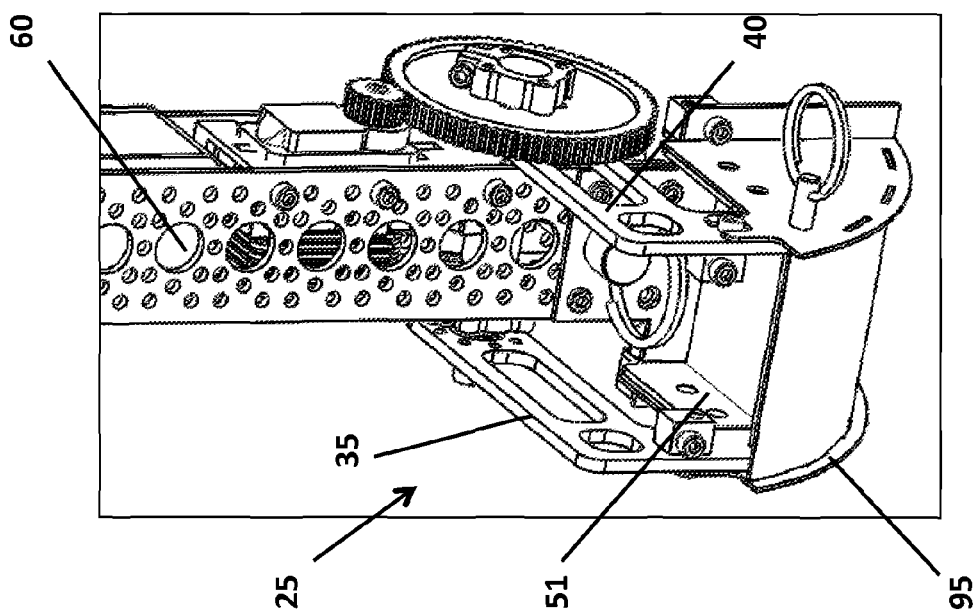
FIG. 6A is a perspective view of the lower portion of the sampling device, detailing pin placement for scoop activation, according to an embodiment of the present invention.
Figure 7:
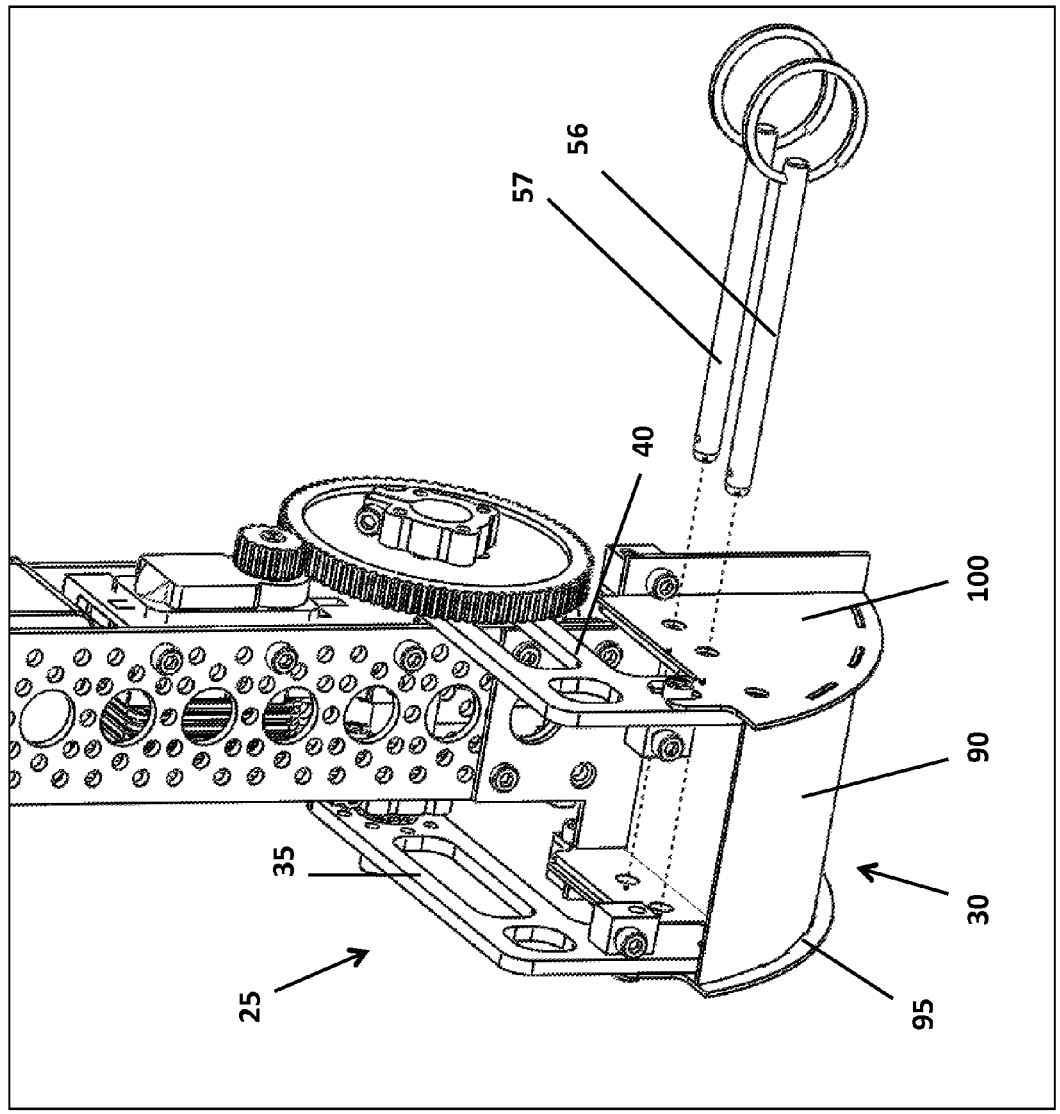
FIG. 7 is a perspective view of the lower portion of the sampling device, detailing pin placement for scoop and spade removal, according to an embodiment of the present invention.

With reference to FIGS. 6A-6B, in an embodiment, spade 50 is attached to tower 10 using at least one bolt 195 that connects through mounting hole 60. In an embodiment, when bolts 195 are not used, pin 58 may be used to connect spade 50 to tower 10 by passing pin 58 through axially aligned holes 190 of spade 50 and tower 10. This embodiment easily allows spade 50 to be detached with scoop 30, forming detachable container 145 (see FIG. 8), without using bolts or screws.

Control System

The control system 115 is also generally housed within the tower, where it is protected by the rigid walls of tower 10. Control system 115 comprises a microcontroller, an inertial measurement unit, a current sensor, a potentiometer, a battery, and at least one transceiver. When commanded, control system 115 sends a signal to control servo 15, and actuate scoop 30 for obtaining a sample.

In a preferred embodiment, control system 115 is implemented with a microcontroller with three analog inputs (ADC inputs) and one digital output; for example, a 16 MHz Arduino Pro Mini. The ADC inputs may be used with the current sensor, potentiometer, and battery. As a result, the microcontroller is given information regarding the servo current drain, servo position, and battery charge. The digital output can be used to send commands to the servo. A set of MEMS inertial sensors comprising an inertial measurement unit may be interfaced with the microcontroller using additional digital inputs and outputs. In a preferred embodiment, an inertial measurement unit is used to provide estimates of orientation of sampling device 5 and determine if it needs to be repositioned. Measured changes of acceleration are used to detect when sampler device 5 is dropped and has touched ground. The inertial measurements may be interpreted by software algorithms to provide the control system with information regarding the static and dynamic orientation of the sampling device. In an embodiment, a distance sensor can be attached to sampling device 5 to determine when it has contacted the ground to take a sample.

A sensor provides feedback on scoop position to control system 115. In a preferred embodiment, the rotary potentiometer is located on the external portion of the channel, attached directly behind the output gear to re-establish the scoop position measurements, allowing a full 360-degree rotation of the gear addition. In another embodiment, the potentiometer is located internally within the tower, allowing only a 90-degree rotation of the gear addition. In an alternative embodiment, a rotary encoder system is used to measure scoop position.

A transceiver can be used to communicate with the ground station computer or remote controller. In other embodiments, multiple transceivers can be used to further eliminate potential communication errors. An example of a preferred transceiver is the Xbee Pro 900HP 900 MHz transceiver with a whip antenna, with a transmission rate of 200 Kbps at a range of 6.5 km. A transceiver is not needed in an embodiment wherein the closing of the scoop is purely mechanical and not electrically actuated, automatically actuated by the sampler controller, or signaled via a connection with the deploying device.

To provide the user with this useful feedback data and a method to input commands, the ground station computer or remote controller may include a user interface. In one embodiment, the system displays data information sequentially in three individual columns, for example, battery voltage (V), servo current drain (mA), and servo position/position feedback (%). For user interaction and control, data is displayed on the console screen and the user inputs the commands as a value in microseconds, which correspond to a servo position (generally, 0-180 degrees). In a preferred embodiment, the servo commands have a separate degree input that only receives degrees and rejects other data. In a preferred embodiment, high level commands (for example, Take Sample) are translated by the ground control computer or control system into sequences of individual tasks for the control system, including sending commands to the server and measuring sensor data. In a preferred embodiment, a real time graphical plot of data such as torque and servo position is displayed to provide a better context of the sampler's condition. Presenting information in real time plots is a superior technique to visualize information, compared to presenting numerical data scrolling down a screen, which can lead to the operator quickly identifying optimal or dangerous operating points and trends. Additionally, at high data rates, a graph shows information more clearly than numbers scrolling down a screen.

In terms of functionality, both the ground station and control system 115 are capable of parsing sensor data and servo commands through the use of software. In an embodiment, when 10 Hz data packets are received at the ground station transceiver, binary data is parsed and verified using cyclic redundancy checks. The microcontroller uses a point-to-point protocol and cyclic redundancy checks. This protocol is used to parse servo commands sent from ground station to ensure that data corruption does not lead to servo malfunctions. Additionally, the microcontroller firmware is written to constrain any commands outside of the servo's physical parameters.

A watertight box may enclose the control system 115. In a preferred embodiment, the box is aluminum and is small enough to fit within the sampler's body. In an embodiment other materials such as plastic or composites may be used to reduce weight. Preferably it is located in a position where the sampler's center of gravity is not greatly affected. For external connections, a pin connector may be installed at the bottom of the box for power or data transmission. The pins may be used to connect sensors and the actuator servo 15 to the control system.

Deploying Device

Figure 9:
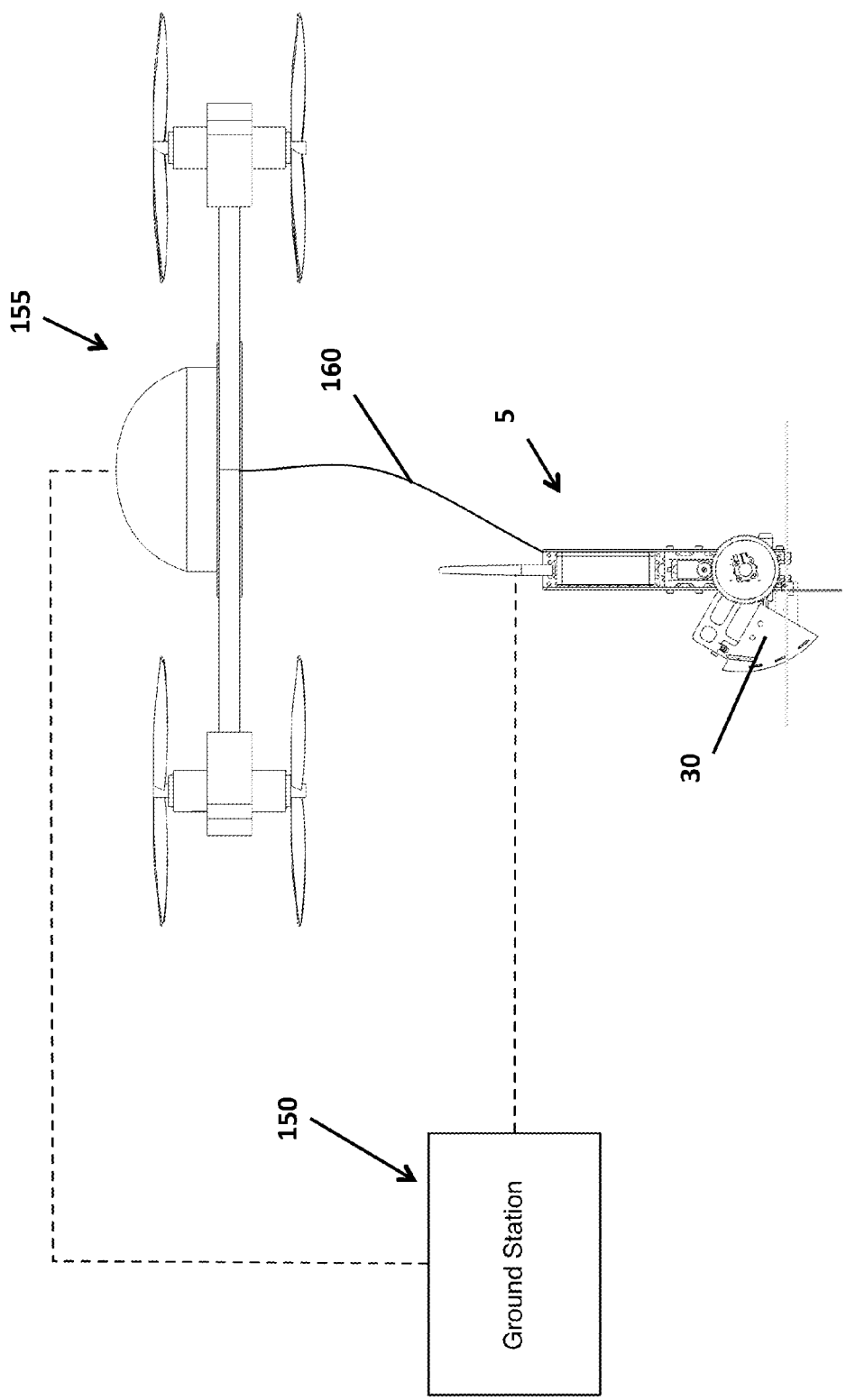
FIG. 9 is a depiction of the system including a sampling device, a ground station, and deploying device, according to an embodiment of the present invention.

With reference to FIG. 9, a preferred embodiment of the system comprising the sampling device 5, including control system 115, a ground station 150, and deploying device 155. Ground station 150 communicates wirelessly (represented by dashed lines) to deploying device 155, a UAV (Unmanned Aircraft Vehicle), for example, and sampling device 5. In this embodiment, the UAV 155 does not communicate with sampling device 5. The operator would use ground station (computer, laptop, tablet, phone, etc) 150 to communicate to the UAV 155 (or fly the UAV with RC transmitter). The operator would use ground station 150 to send commands and receive data from the sampler. The "release" signal is sent to the UAV 155, which releases the sampling device 5.

At the ground station 150, GPS locations are entered into the deploying device 155, for example, a UAV autopilot flight plan, along with other parameters such as velocity and altitude. Once the UAV 155 has successfully flown to a sampling location with the sampling device 5 attached beneath, it will hover and wait for a ground station command, or automatically deploy the sampling device 5. To deploy the sampling device 5 on the surface below, a drop and pull method is utilized, similar to how helicopters use fire buckets. Sending a message or command from the ground station 150 will command the UAV onboard controller to detach the entire sampling device 5 from the frame of the UAV 155. The sampling device 5 then lands flat on the surface of the tailings deposit, for example, below and encapsulates the sample using its scoop 30. Afterwards, the entire sampling device 5 is pulled vertically upward and out of the tailings using a tether 160 attached to the UAV 155. The UAV 155 then returns the sample by maintaining a stabilized flight back to the ground station 150, where the sample can be removed from the sampling device 5 and the sampling device 5 can be reset for another use.

In other embodiments the ground station 150 communicates only to UAV 155, then UAV 155 communicates to sampler. In another embodiment the UAV 155 is completely autonomous, and the ground station 150 only communicates to sampler. In another embodiment, the sampling device 5 is autonomous, obviating the need for ground station 150.

In a preferred embodiment, the deploying device 155 is an Unmanned Aerial Vehicle (UAV) that has vertical take-off and landing capability, such as a quadcopter; however, the deploying device can also be a crane or anything that can deploy the sampling device 5 to obtain samples from tailings deposits at various locations. The flight time, payload capacity, stability, and leadtime should all be considered when choosing a transportation or deployment device of the sampling device 5. In a preferred embodiment, the deploying device is capable of hovering, as the sampling device 5 is to be dropped and retrieved within the same flight. In a preferred embodiment, the deploying device 155 is a multi-rotor system with high stability and hovered flight, as multi-rotor systems have more control surfaces and thus, it is capable to maintain effective orientation in high wind missions. In various embodiments, different multi-rotor UAVs may be used depending on the desired monetary cost, flight time, payload capacity, whether a heavy design concept is required, and whether a GPS or autopilot system is desired. Examples of such multi-rotor UAV's include the DJI S1000, DJI S1000 Premium with A2 Autopilot, Turbo Ace Matrix-S, ELEV-8 Quad-copter, Streak 1000 OctoCopter, Cyclone X8 Octocopter, and Streak 800 Pro V2 Hexacopter. In other embodiments, the deployment vehicle may be manned or unmanned, and the sampler may be deployed by a crane, hovercraft, boat or other similar means for vertical deployment.

Figure 10:
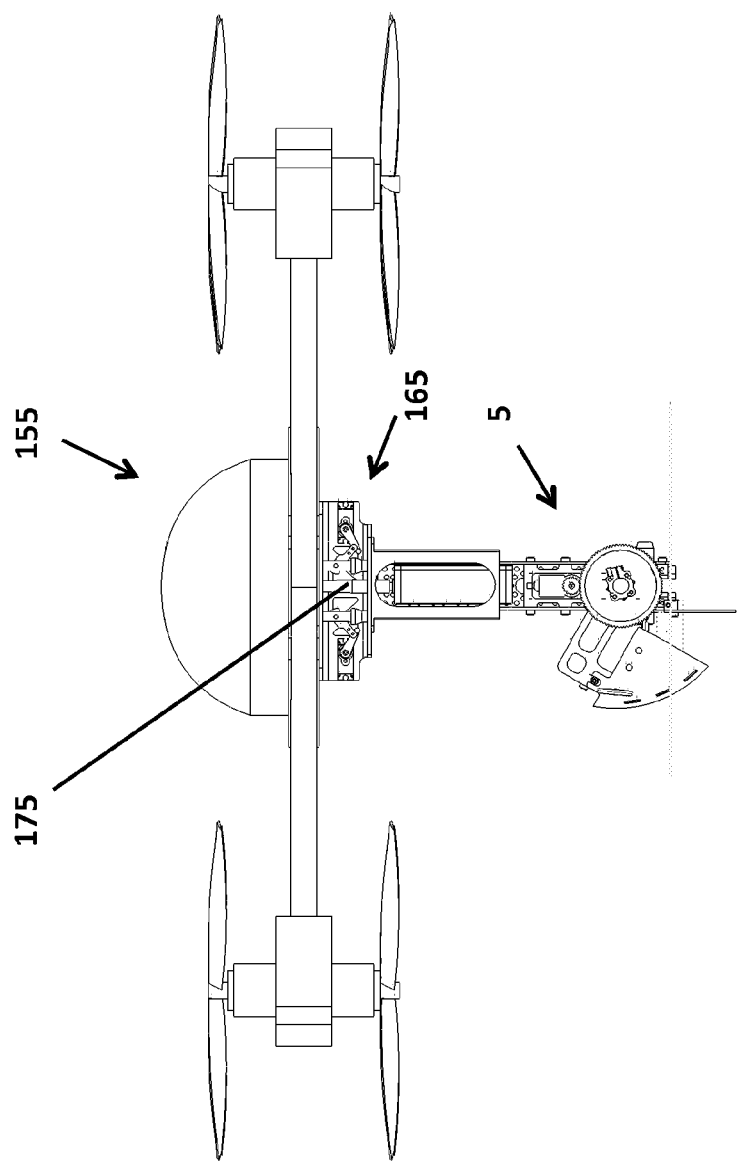
FIG. 10 is a side view of a deploying device using a release mechanism to release the sampling from the deploying device, according to an embodiment of the present invention.

FIG. 10 shows an embodiment where a tether release system 165 is incorporated to release sampling device 5 from deploying device 155 in a situation such as when sampling device 5 might become stuck within the pond. The release mechanism 165 has an aperture to accommodate the antenna 175 so sampling device 5 sits flush against the bottom of the UAV 155. In another embodiment, the antenna 175 can be position on a side of the sampling device.

In a preferred embodiment, the release mechanism is a winch system, employed to drop the sampling device, lowering the impact force of falling sampler and thus, preventing initial sinking. This winch may be a servo gear system attached to the bottom of the UAV that drops the sampling device at a controlled rate. In a preferred embodiment, a servo motor protection case is incorporated to prevent moisture damage in the case of full submerging.

Figure 11:
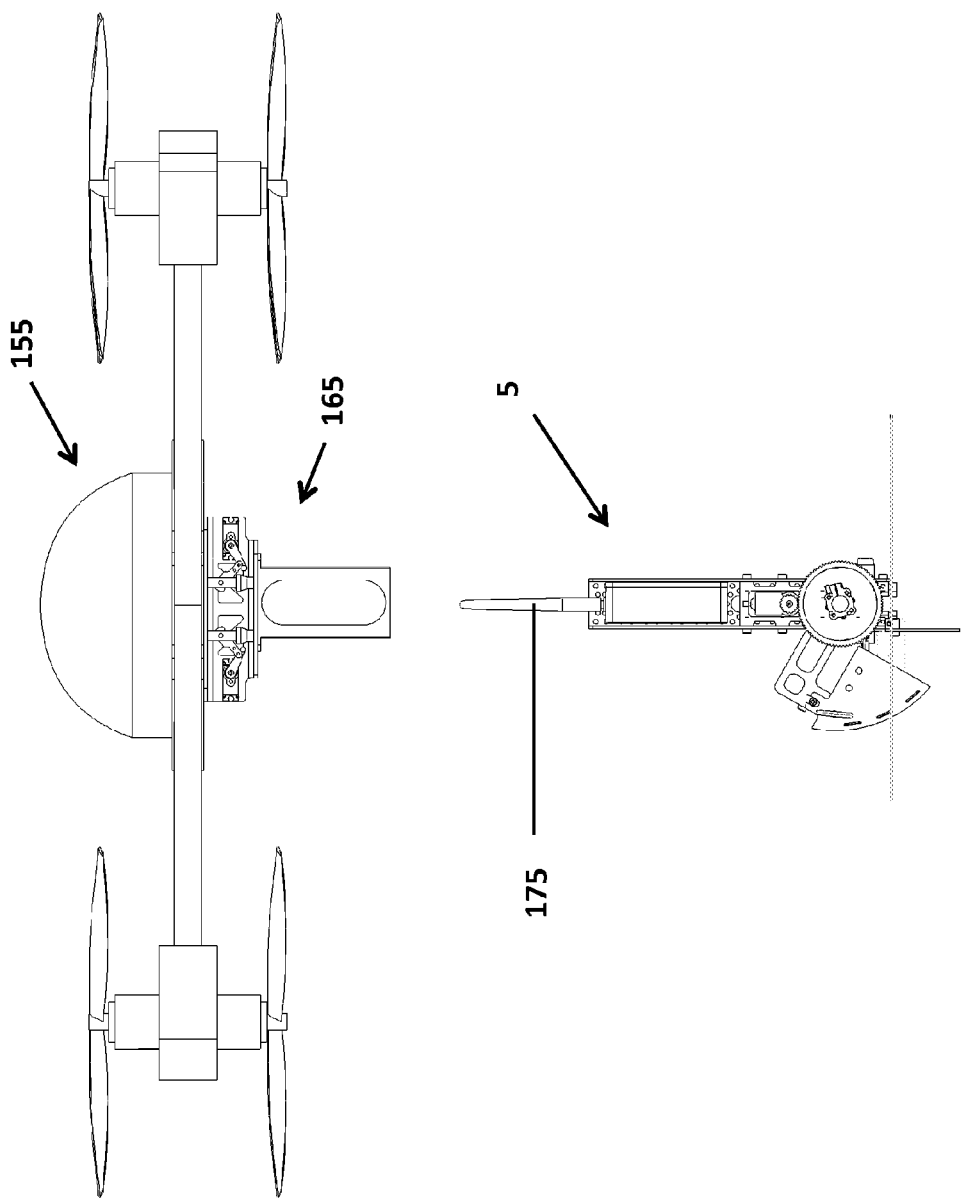
FIG. 11 is a side view of a deploying device using a release mechanism to release the sampling from the deploying device, where the sampling device is detached from the deploying device without the use of a tether, according to an embodiment of the present invention.

FIG. 11 shows an embodiment in which the sampling device 5 is dropped from release system 165 without a tether cable, and then retrieved by the UAV 155 using a release mechanism 165 via communication with the antenna 175. In an embodiment, rather than using an antenna 175, the UAV 155 can include a cable, or light pole with a hook to retrieve the sampling device 5.

Figure 12:
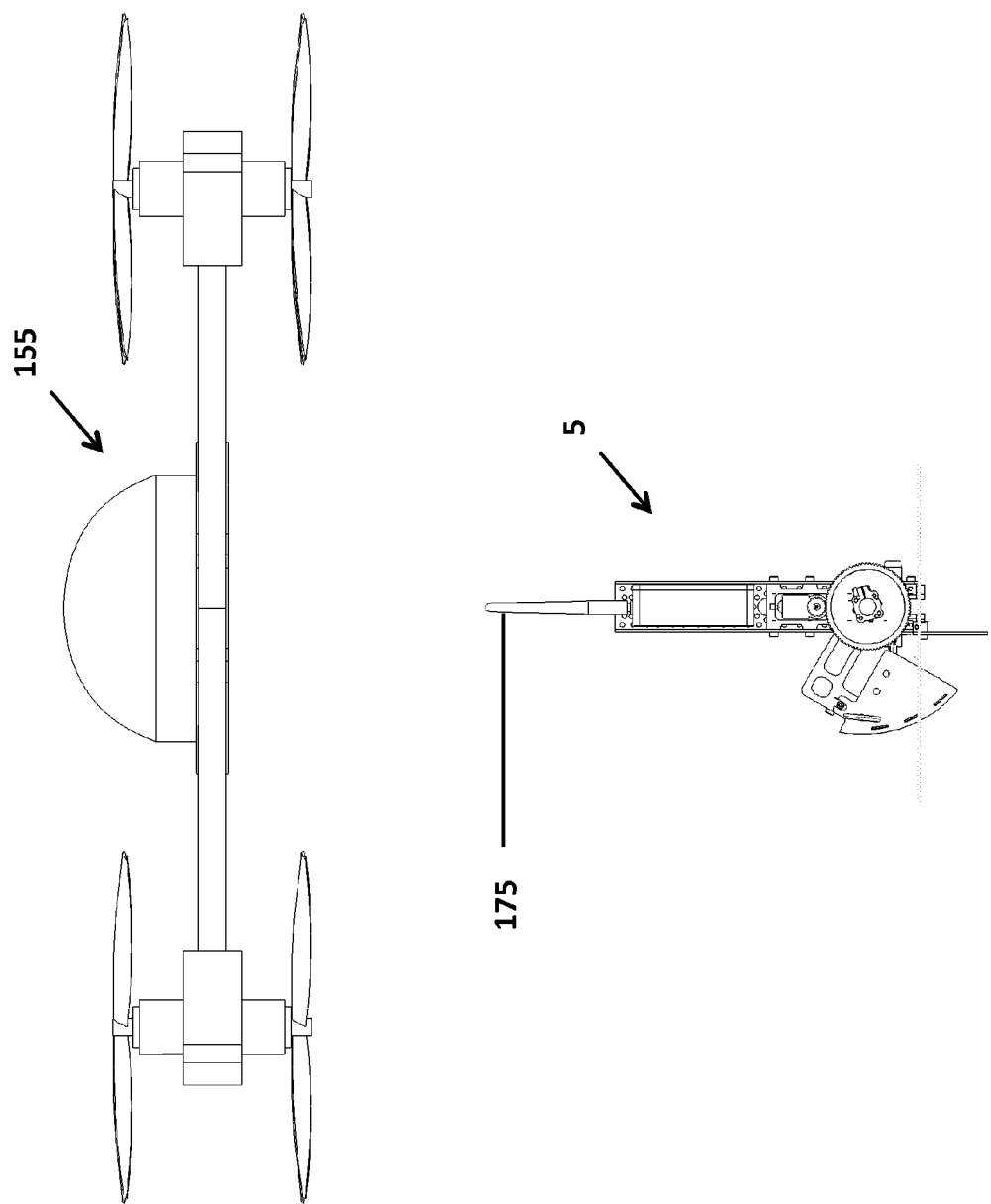
FIG. 12 is a side view of a deploying device, where the sampling device is detached from the deploying device without the use of a tether, according to an embodiment of the present invention.

FIG. 12 shows an embodiment in which the sampling device 5 is dropped without a tether cable, and then retrieved by the UAV 155 via communication with the antenna 175. In an embodiment, rather than using an antenna 175, the UAV 155 can include a cable, or light pole with a hook to retrieve the sampling device.

Figure 13:
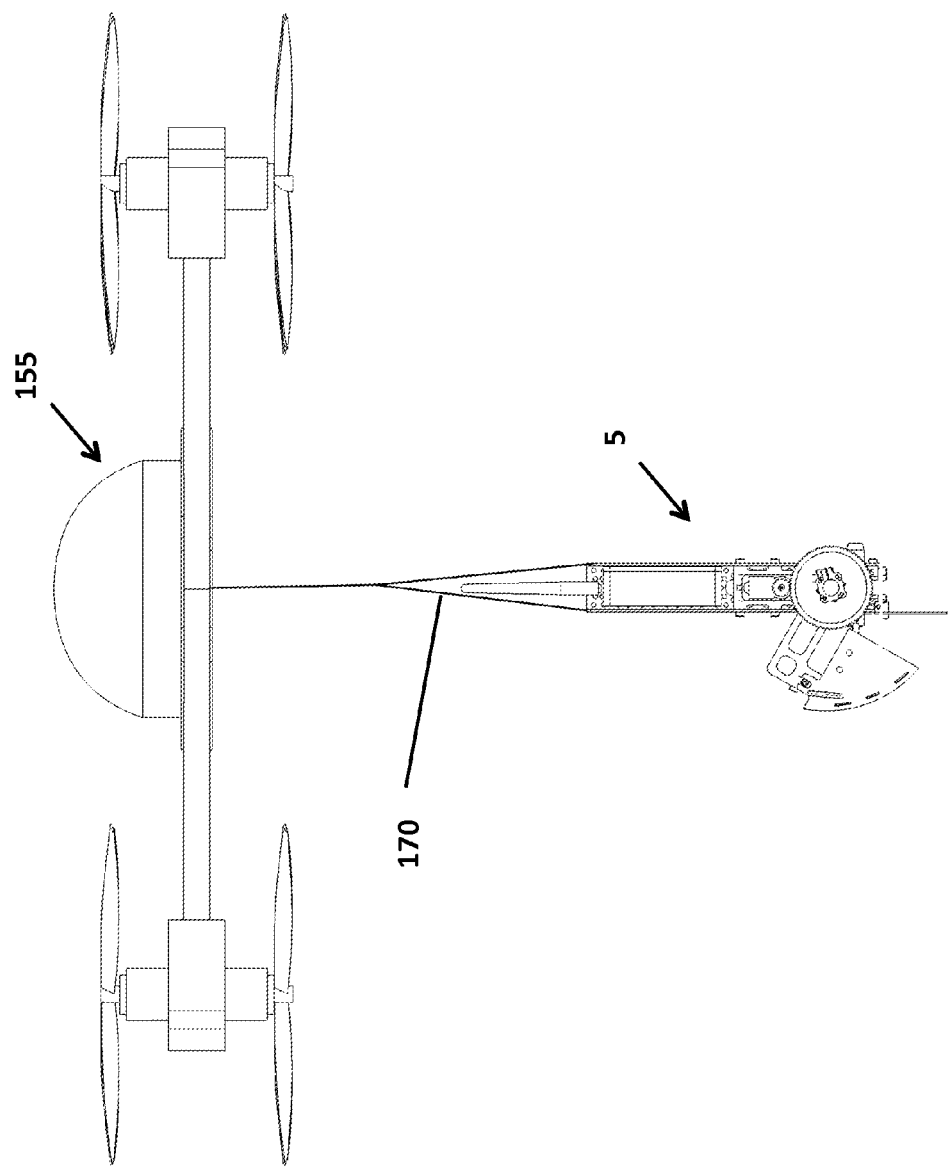
FIG. 13 is a side view of a deploying device that deploys the sampling device through the use of a split rope or cable, according to an embodiment of the present invention.
Figure 14:
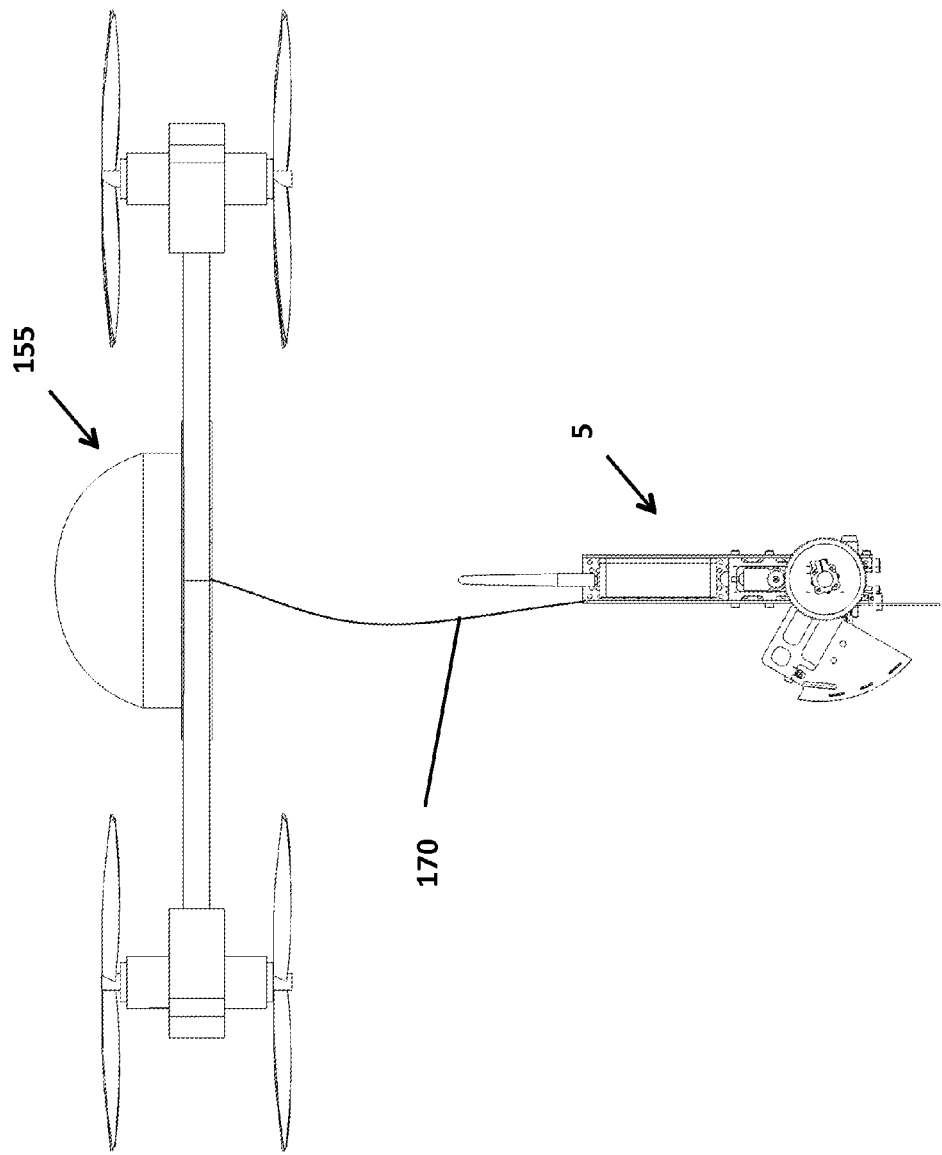
FIG. 14 is a side view of a deploying device that deploys the sampling device through the use of a rope or cable, according to an embodiment of the present invention.

FIGS. 13 and 14 show other embodiments where a cable or rope 170 will hold the sampling device 5 to the UAV 155.

Figure 15:
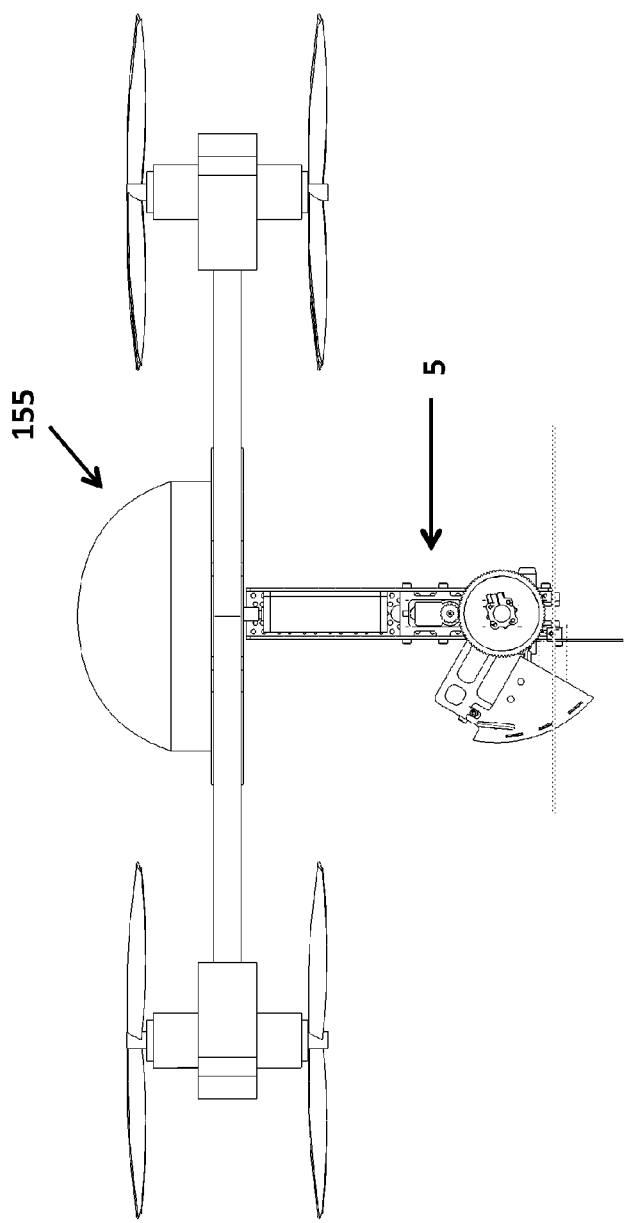
FIG. 15 is a side view of a deploying device that holds the sampling device flush to the deploying device, according to an embodiment of the present invention.

With reference to FIG. 15, a mechanism to tension the cable (not shown) inside the UAV 155 holds the sampling device 5 flush to the UAV 155. In this embodiment, the sampling device 5 has a top surface of flush against the UAV 155, so that it does not swing too much (might cause stability issues). The cable (not shown) that holds the sampler could provide the tension required to keep it flush, which may be facilitated by the winch, for example. Once the sampling device 5 is released, the cable can be used to winch the sampling device back up. In an embodiment that does not use a winch, the sampling device 5 can be left hanging, as shown in FIGS. 9, 13, and 14.

Applications of the sampling device are not limiting to retrieval of samples (soil, water, vegetation) (disturbed and undisturbed surface), but may also include taking measurements at close range with a sensor carried to the location; shear strength; delivering a wireless sensor; sensor placement; pollinating flowers or delivering chemicals to difficult to reach locations.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

We claim:

1. A sampling device for retrieving a sample comprising:
   a. a frame;
   b. a scoop having an open end configured to retrieve a sample;
   c. an actuator in communication with the scoop;
   d. a base plate mounted below the frame, configured to support the sampling device on the material; and
   e. a spade at least as large as the open end, extending below the base plate, configured to extend into the material and configured to engage with the open end of the scoop once a sample have been retrieved,
   wherein the actuator is configured to move the scoop between an open and a closed position, and in the open position, there is a gap between the open end of the scoop and the spade for the entry of a sample, and in the closed position, the open end of the scoop sealingly engages with the spade to close the scoop and retain the retrieved sample.

2. A sampling device as in claim 1, further comprising:
   a. a shaft; and
   b. at least one moment arm, each moment arm having a first end and a second end, wherein the first end is attached to the scoop and the second end is attached to the shaft, wherein the actuator rotates the shaft, causing the moment arm(s) to move the scoop between the open and closed positions.

3. A sampling device as in claim 1, further comprising:
   a. an unmanned aerial vehicle; and
   b. a tether connecting the aerial vehicle and the sampling device,
   wherein the unmanned aerial vehicle is configured to transport the sampling device to areas of low soil bearing strength, where it deploys and retrieves the sampling device using the tether.

4. A sampling device as in claim 1, further comprising:
   a. an unmanned aerial vehicle; and
   b. a winch, attached to the unmanned aerial vehicle,
   wherein the unmanned aerial vehicle is configured to transport the sampling device to areas of low soil bearing strength, where it deploys and retrieves the sampling device using the winch.

5. A sampling device as in claim 3, further comprising:
   a. an antenna attached to the sampling device;
   b. an antenna attached to the unmanned aerial vehicle; and
   c. a radio-frequency-enabled remote ground station,
   wherein the sampling device, the unmanned aerial vehicle, and the ground station communicate with one another through radio frequency.

6. The sampling device as in claim 1, further comprising rubber protrusions affixed to the spade that correspond with the open end of the scoop.

7. The sampling device as in claim 1, wherein the base plate has cut-outs configured for reducing wind resistance.

8. The sampling device as in claim 1, further comprising a suction-eliminating layer on the underside of the base plate, the layer selected from the group consisting of a rubber membrane, a hydrophobic coating and a disposable paper liner.

9. The sampling device as in claim 1, wherein at least a portion of the base plate is constructed of a lightweight and buoyant material.

10. The sampling device of claim 1, further comprising at least one moment arm connected between the scoop and the actuator for rotating the scoop from an open to a closed position.

11. The sampling device of claim 10, wherein there are two moment arms.

12. The sampling device of claim 1, wherein the scoop closes against the spade, forming a container.

13. The sampling device of claim 12, wherein the container is removable from the sampling device.

14. The sampling device of claim 12, wherein the container is self-enclosing.

15. The sampling device of claim 1, further comprising a detachable cover on the bottom of baseplate, configured to reduce suction between the baseplate and the material.

16. The sampling device of claim 15, wherein the detachable cover is biodegradable.

17. The sampling device of claim 1, further comprising an antenna that communicates with a ground station to signal the actuator to move the scoop.

18. The sampling device of claim 1, wherein the sampling device is aerially deployable and retrievable by an aircraft capable of hovering.

19. The sampling device of claim 1, wherein the sampling device is remotely deployable and retrievable from impassable locations.

20. The sampling device of claim 1, wherein the impassable locations have low bearing strength soils.

* * * * *